US006945999B2

(12) United States Patent
Schneider et al.

(10) Patent No.: US 6,945,999 B2
(45) Date of Patent: Sep. 20, 2005

(54) IMPLANTABLE HEARING AID TRANSDUCER WITH ACTUATOR INTERFACE

(75) Inventors: Robert Edwin Schneider, Erie, CO (US); Scott Allan Miller, III, Lafayette, CO (US)

(73) Assignee: Otologics LLC, Boulder, CO (US)

( * ) Notice: Subject to any disclaimer, the term of this patent is extended or adjusted under 35 U.S.C. 154(b) by 208 days.

(21) Appl. No.: 10/351,743

(22) Filed: Jan. 27, 2003

(65) Prior Publication Data

US 2004/0148025 A1 Jul. 29, 2004

(51) Int. Cl.[7] ............................ A61F 2/18; H04R 25/00
(52) U.S. Cl. ............................................ 623/10; 600/25
(58) Field of Search ............................ 623/10; 600/25; 607/55–57; 381/68.3, 312

(56) References Cited

U.S. PATENT DOCUMENTS 5,558,618 A * 9/1996 Maniglia ..................... 600/25
5,899,847 A 5/1999 Adams et al. ................ 600/25
6,315,710 B1 * 11/2001 Bushek et al. ................ 600/25
6,398,717 B1 * 6/2002 Leysieffer et al. ............ 600/25
6,629,922 B1 * 10/2003 Puria et al. ................... 600/25

OTHER PUBLICATIONS

U.S. Appl. No. 10/351,699, entitled “Implantable Hearing Aid Transducer with Advanceable Actuator to Facilitate Coupling with the Auditory System”, filed on Jan. 27, 2003.

U.S. Appl. No. 10/351,682, entitled “Apparatus for Connection of Implantable Devices to the Auditory System”, filed on Jan. 27, 2003.

U.S. Appl. No. 10/394,499, entitled Improved Apparatus and Method for Ossicular Fixation of Implantable Hearing Aid Actuator, filed on Mar. 20, 2003.

* cited by examiner

*Primary Examiner*—David J. Isabella
(74) *Attorney, Agent, or Firm*—Marsh Fischmann & Breyfogle LLP

(57) ABSTRACT

An implantable hearing aid transducer that compensates in situ for undesirable interfaces with a middle ear component. The transducer includes a housing, an actuator, a driver, and an actuator interface. According to one embodiment, the actuator interface is reshapeable in situ from a first shape to a second shape to permit movement of one of the actuator and the middle ear component in at least a first dimension to compensate for loading pressure. In this regard, the actuator interface may be gradually deformable to permit the movement of the transducer and/or the middle ear component, as well as, resistive to sudden movements of the actuator such that vibration at acoustic frequencies occurs between the actuator and the middle ear component.

26 Claims, 5 Drawing Sheets

IMPLANTABLE HEARING AID TRANSDUCER WITH ACTUATOR INTERFACE

FIELD OF THE INVENTION

The invention is related to the field of hearing aids, and in particular, to an implantable transducer that includes an actuator interface to minimize loading of a middle ear component by the transducer.

BACKGROUND OF THE INVENTION

Implantable hearing aids entail the subcutaneous positioning of some or all of various hearing augmentation componentry on or within a patient's skull, typically at locations proximate the mastoid process. Implantable hearing aids may be generally divided into two classes, semi-implantable and fully implantable. In a semi-implantable hearing aid, components such as a microphone, signal processor, and transmitter may be externally located to receive, process, and inductively transmit a processed audio signal to implanted components such as a receiver and transducer. In a fully-implantable hearing aid, typically all of the components, e.g., the microphone, signal processor, and transducer, are located subcutaneously. In either arrangement, a processed audio signal is provided to a transducer to stimulate a component of the auditory system By way of example, one type of implantable transducer includes an electromechanical transducer having a magnetic coil that drives a vibratory actuator. The actuator is positioned to mechanically stimulate the ossicles via physical engagement. (See e.g., U.S. Pat. No. 5,702,342). In this regard, one or more bones of the ossicles are made to mechanically vibrate, causing the vibration to stimulate the cochlea through its natural input, the so-called oval window. An example of this transducer is included in the MET™ hearing aid of Otologics, LLC, in which a small electromechanical transducer is used to vibrate the incus (the 2nd of the 3 bones forming the ossicles), and thence produce the perception of sound. In this case, the vibratory actuator is coupled to the ossicles during mounting and positioning of the transducer within the patient. In one example, such coupling may occur via a small aperture formed in the incus bone.

As will be appreciated, coupling with the ossicles poses numerous challenges. For instance, during positioning of the transducer, it is often difficult for an audiologist or surgeon to determine the extent of the coupling. In other words, how well the actuator is attached to the ossicles. Additionally, due to the size of the transducer relative to the ossicles, it is difficult to determine if loading exists between the ossicles and transducer. In this regard, precise control of the engagement between the actuator of the transducer and the ossicles is of critical importance as the axial vibrations can only be effectively communicated when an appropriate interface or load condition exists between the transducer and the ossicles. Overloading or biasing of the actuator can result in damage or degraded performance of the biological aspect (movement of the ossicles) as well as degraded performance of the mechanical aspect (movement of the vibratory member). Additionally, an underloaded transducer, e.g., where the actuator is not fully connected to the ossicles, may result in reduced performance of the transducer.

Another difficulty with such coupling is that in some cases patients can experience a "drop-off" in hearing function after implantation. Such a drop off may be caused by changes in the physical engagement of the actuator, e.g., due to things such as tissue growth, or may be caused by a malfunction of the transducer or other componentry. After implantation, however, it is difficult to readily assess the performance and/or adjust an implanted transducer and interconnected componentry. For example, in the event of a "drop-off" in hearing function after implantation, it is difficult to determine the cause, e.g., over/under loading of the interface due to tissue growth or some other problem with the hearing aid, without invasive and potentially unnecessary surgery. In addition, once coupled for an extended period, the maintenance and/or replacement with a next generation transducer may be difficult.

SUMMARY OF THE INVENTION

In view of the foregoing, a primary object of the present invention is to simplify and improve implantation procedures for implantable hearing aid transducers. Another object of the present invention is to improve coupling of implantable transducers with a middle ear component, such as the ossicles. Another object of the present invention is to provide a means for achieving a proper interface, e.g., a low mechanical bias or no-load interface, between an implanted hearing aid transducer and a component of the auditory system. A related object of the present invention is to provide an implantable hearing aid transducer with the ability to compensate in situ for undesirable interfaces both during implantation and subsequent to implantation. In the context of the present invention, "in situ," refers to in its proper position, e.g., in the context of the present transducer, as implanted in a patient and coupled to a middle ear component.

In relation to a transducer according to the present invention, each of the various aspects discussed in more detail below may include a transducer body preferably constructed from a biocompatible material that is implantable within a patient. The transducer may also generally include an actuator associated with the transducer body to stimulate a component of the middle ear. The transducer may also include a driver to drive the actuator in response to transducer drive signals received from a signal processor. The driver may be of any suitable design to drive the actuator and associated middle ear component to produce or enhance the sensation of sound for the patient. For instance, some examples of the driver may include without limitation, an electrical, piezoelectric, electromechanical, and/or electromagnetic driver.

One or more of the above objectives and additional advantages may be realized by a first aspect of the present invention, which provides an implantable hearing aid transducer having an actuator interface. The actuator interface is reshapeable in situ from a first shape to a second shape to permit movement of one of the actuator or the middle ear component in at least a first dimension. Advantageously, such in situ movements improve coupling between the actuator and the middle ear component, e.g., by permitting gradual movement of the actuator or the middle ear component to reduce loading pressures.

Various refinements exist of the features noted in relation to the subject first aspect of the present invention. Further features may also be incorporated in the subject first aspect as well. These refinements and additional features may exist individually or in any combination. For instance according to one feature of the present aspect, the actuator interface may be located at various positions relative to the actuator as a matter of design choice. In one example, the interface may be located between the actuator and the middle ear component. In another example, the interface may be located between a first portion of the actuator and a second portion of the actuator. In yet another example, the interface may form at least a portion of an interconnection of the actuator to the transducer.

According to another feature of the present aspect, the actuator interface may be reshapeable from the first shape to the second shape to permit movement in a second dimension of one of the actuator or the middle ear component to relieve loading pressures.

According to another feature of the present aspect, the actuator interface may be configured to automatically reshape in response to a steady state application of pressure from the middle ear component to permit movement in at least the first dimension of one of the actuator or the middle ear component. The automatic movement may occur during or shortly after implantation of the transducer to compensate for loading pressures resulting from the implant procedure. Furthermore, the automatic movement may continue during the life of the implant such that the transducer continually compensates for changing aspects of the implant, e.g., biological changes such as tissue growth. In this case, the interface may be a material with the ability to "cold flow" at body temperature, e.g., in the range of 94° to 108°, when subjected to a pressure above a predetermined threshold, yet includes sufficient viscosity at body temperature to conduct vibrations at acoustic frequencies. Some examples of such materials may include without limitation, wax based materials, elastomer based materials, and/or silicon based materials. In the context of the present application, the terms "cold flow" or "cold flowing" refer to materials having the ability to deform under a steady state or substantially steady state application of pressure without the introduction of a stimulus.

According to another feature of the present aspect, the actuator interface may be configured to reshape in response to a stimulus. In this case, the actuator interface may be a material that is selectively transformable from a first state, e.g., a liquid or gel, to a second state, e.g., substantially solid, using a stimulus such as heat, laser energy, chemical catalyst, or other appropriate stimulus. According to this characterization, during the implant procedure and subsequent to relaxation of any loading pressures on the middle ear component by the transducer, the stimulus may be introduced to solidify or substantially solidify the actuator interface and secure the actuator in position relative to the middle ear component.

In an alternative feature of the present aspect, the actuator interface may be selectively transformable from an initially soft state to a second state of sufficient viscosity at body temperature to conduct vibrational energy. In other words, the material may initially be a liquid or gel at body temperature to permit relatively free movement of the actuator during the implant procedure. Subsequent to the implant procedure, the material may be selectively transformable to a higher, viscosity material that transmits vibrations at audible frequencies but is still reshapeable to permit gradual movement of one of the actuator or the middle ear component.

In yet another alternative feature of the present aspect, the actuator interface may be a material that is selectively transformable from a substantially solid state to a deformable state, and again selectively transformable back to the substantially solid state, through the introduction of one or more stimuli. In this regard, the actuator may be initially rigidly fixed to the transducer by the actuator interface to facilitate attachment to the middle ear component. Subsequent to the attachment, the actuator interface may be transformed to the deformable state to permit movement of the actuator and relaxation of loading pressures. The actuator interface may then again be transformed back to the substantially solid state to secure the actuator relative to the middle ear component.

One or more of the above objectives and additional advantages may also be realized by a second aspect of the present invention, which provides a method for preventing loading of a middle ear component by an implantable hearing aid transducer. The method includes the steps of coupling an actuator of the transducer to the middle ear component. In response to a pressure applied on the actuator by the middle ear component, the method includes the step of reshaping an actuator interface from a first position to a second position to permit movement of one of the actuator or the middle ear component in at least a first dimension.

Various refinements exist of the features noted in relation to the subject second aspect of the present invention. Further features may also be incorporated in the subject second aspect as well. These refinements and additional features may exist individually or in any combination. For instance according to one feature of the present aspect, the reshaping step may include automatically reshaping the actuator interface from the first shape to the second shape in response to a steady or substantially steady pressure. According to another feature of the present aspect, the reshaping step may include reshaping the actuator interface in response to pressure if the pressure is above a predetermined threshold. According to another feature of the present aspect, the reshaping step may include providing a stimulus to the actuator interface to initiate the reshaping from the first shape to the second shape.

According to another feature of the present aspect, the method may further include transforming the actuator interface from a solid state to a deformable state responsive to a stimulus. In an alternative feature according to the present aspect, the method may include transforming the actuator interface from a solid state to a deformable state responsive to a stimulus. According to another feature of the present aspect, the reshaping step may include reshaping the actuator interface from the first shape to the second shape to permit movement of one of the actuator and the middle ear component in a second dimension.

One or more of the above objectives and additional advantages may also be realized by a third aspect of the present invention, which provides a hearing aid that includes an acoustic signal receiver, signal processor, and implantable transducer. The acoustic signal receiver is operable to receive acoustic sound and generate acoustic response signals for the signal processor. The signal processor, in turn, is operable to process the acoustic response signals to generate transducer drive signals. The transducer includes an actuator interface that is reshapeable in situ from a first shape to a second shape to permit movement of one of the actuator and the middle ear component in at least a first dimension. In this regard, the transducer may be any one of the above-described embodiments according to the present principles.

Various refinements exist of the features noted in relation to the subject third aspect of the present invention. Further features may also be incorporated in the subject third aspect as well. These refinements and additional features may exist individually or in any combination. For instance according to one feature, the present hearing aid may be a fully or semi-implantable hearing aid. In semi-implantable hearing aid applications, the acoustic sounds may be inductively coupled to the implanted transducer via an external transmitter and implanted receiver. In fully implantable applications, the acoustic sounds may be received by an implanted acoustic signal receiver e.g., an omni-directional microphone, and provided to an implanted signal processor for generation of the transducer drive signals. Additional aspects, advantages and applications of the present invention will be apparent to those skilled in the art upon consideration of the following.

DETAILED DESCRIPTION

Reference will now be made to the accompanying drawings, which at least assist in illustrating the various pertinent features of the present invention. Although the present invention will now be described primarily in conjunction with semi-implantable hearing aid systems, it should be expressly understood that the present invention is not limited to this application, but rather, only to applications where positioning of an implantable device within a patient is required.

Figure 1:
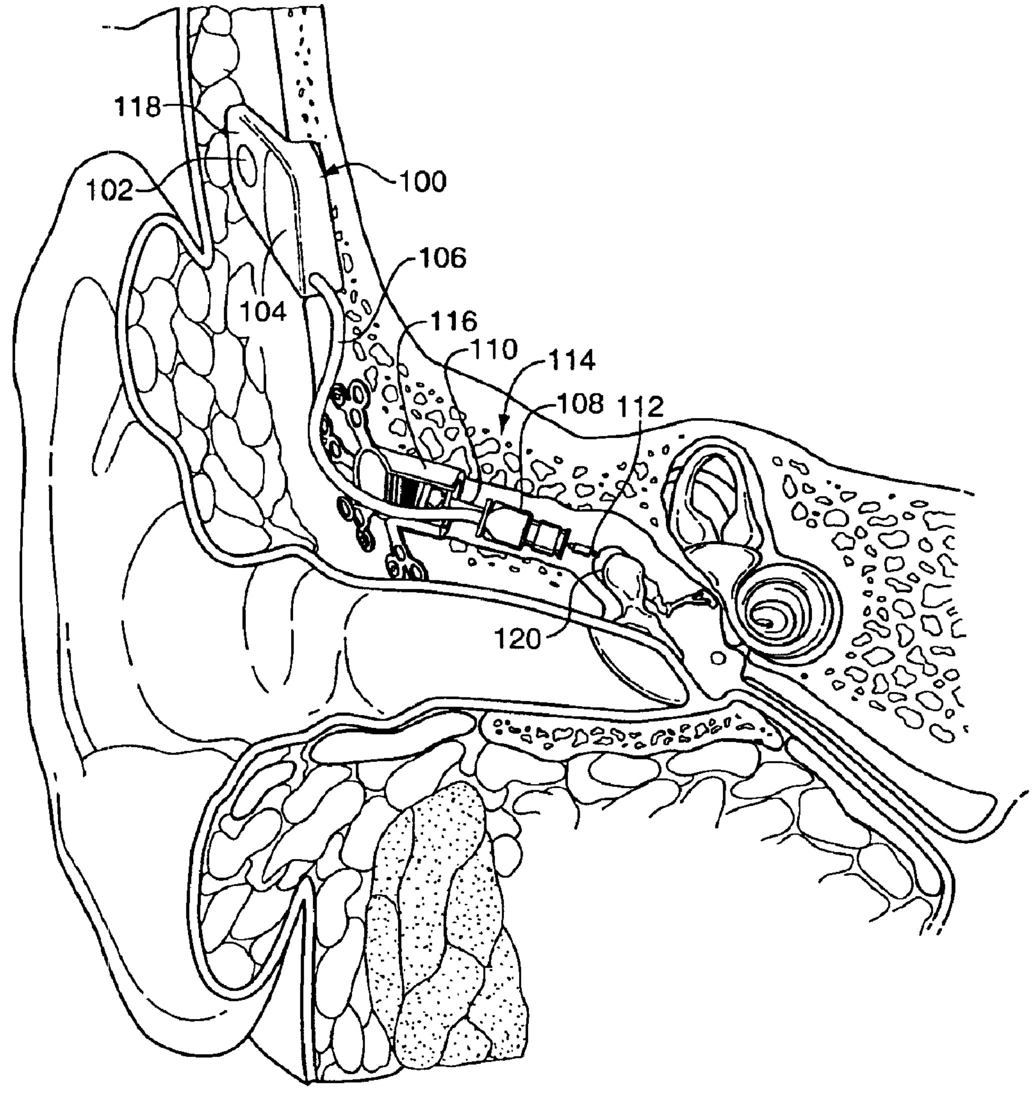
FIGS. 1 and 2 illustrate implantable and external componentry respectively, of a semi-implantable hearing aid system according to the present invention.
Figure 2:
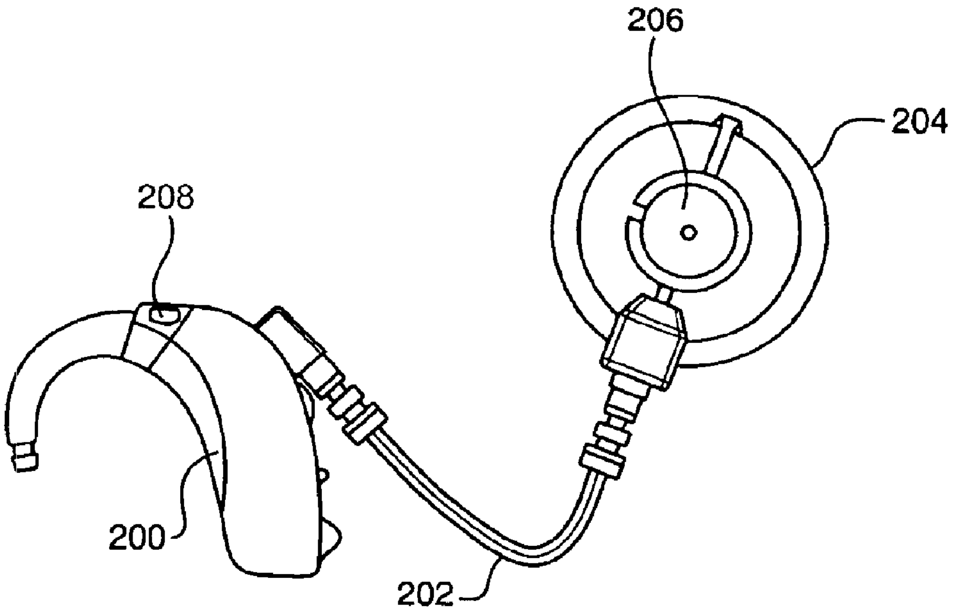

Hearing Aid System:

FIGS. 1 and 2 illustrate one application of the present invention. The illustrated application comprises a semi-implantable hearing aid system having implanted components shown in FIG. 1, and external components shown in FIG. 2. As will be appreciated, the present invention may also be employed in conjunction with fully implantable systems, wherein all components of a hearing aid system are located subcutaneously.

In the illustrated system, an implanted biocompatible housing 100 is located subcutaneously on a patient's skull. The housing 100 includes an RF signal receiver 118 (e.g., comprising a coil element) and a signal processor 104 (e.g., comprising processing circuitry and/or a microprocessor). The signal processor 104 is electrically interconnected via wire 106 to an electromechanical transducer 108. As will become apparent from the following description, various processing logic and/or circuitry may also be included in the housing 100 as a matter of design choice.

The transducer 108 is supportably connected to a positioning system 110, which in turn, is connected to a bone anchor 116 mounted within the patient's mastoid process (e.g., via a hole drilled through the skull). The electromechanical transducer 108 includes a vibratory member 112 for transmitting axial vibrations to a member of the ossicles of the patient (e.g., the incus 120).

Referring to FIG. 2, the semi-implantable system further includes an external housing 200 comprising a microphone 208 and internally mounted speech signal processing (SSP) unit (not shown). The SSP unit is electrically interconnected via wire 202 to an RF signal transmitter 204 (e.g., comprising a coil element). The external housing 200 is configured for disposition around the rearward aspect of the patient's ear. The external transmitter 204 and implanted receiver 118 each include magnets, 206 and 102, respectively, to facilitate retentive juxtaposed positioning.

During normal operation, acoustic signals are received at the microphone 208 and processed by the SSP unit within external housing 200. As will be appreciated, the SSP unit may utilize digital processing to provide frequency shaping, amplification, compression, and other signal conditioning, including conditioning based on patient-specific fitting parameters. In turn, the SSP unit via wire 202 provides RF signals to the transmitter 204. Such RF signals may comprise carrier and processed acoustic drive signal portions. The RF signals are transcutaneously transmitted by the external transmitter 204 to the implanted receiver 118. As noted, the external transmitter 204 and implanted receiver 118 may each comprise coils for inductive coupling signals therebetween.

Upon receipt of the RF signals, the implanted signal processor 104 processes the signals (e.g., via envelope detection circuitry) to provide a processed drive signal via wire 106 to the electromechanical transducer 108. The drive signals cause the vibratory member 112 to axially vibrate at acoustic frequencies to effect the desired sound sensation via mechanical stimulation of the ossicles of the patient.

As will be discussed in more detail below, the drive signals may be provided to a coil positioned about a cantilevered, conductive leaf member within the electromechanical transducer 108, wherein such leaf member is physically interconnected to the vibratory member 112. The modulating drive signals yield a changing magnetic field at transducer 108, thereby effecting movement of the leaf member and axial movement or vibration of the vibratory member 112. As will also be appreciated, the axial vibrations can only be effectively communicated to the ossicles when an appropriate interface exists (e.g., preferably a no-load interface), between the vibratory member 112 and the ossicles (e.g., via the incus 120). That is, if a desirable mechanical interface has been established (e.g., a no-load physical engagement with a fibrous union), the vibratory member 112 will readily communicate axial vibrations to the ossicles of the patient. On the other hand, if the vibratory member 112 is "underloaded" (no interconnection has been established), axial vibrations may not be communicated. Further, if the vibratory member 112 is "overloaded" against the ossicles, axial vibration transmission may be adversely effected.

Figure 3:
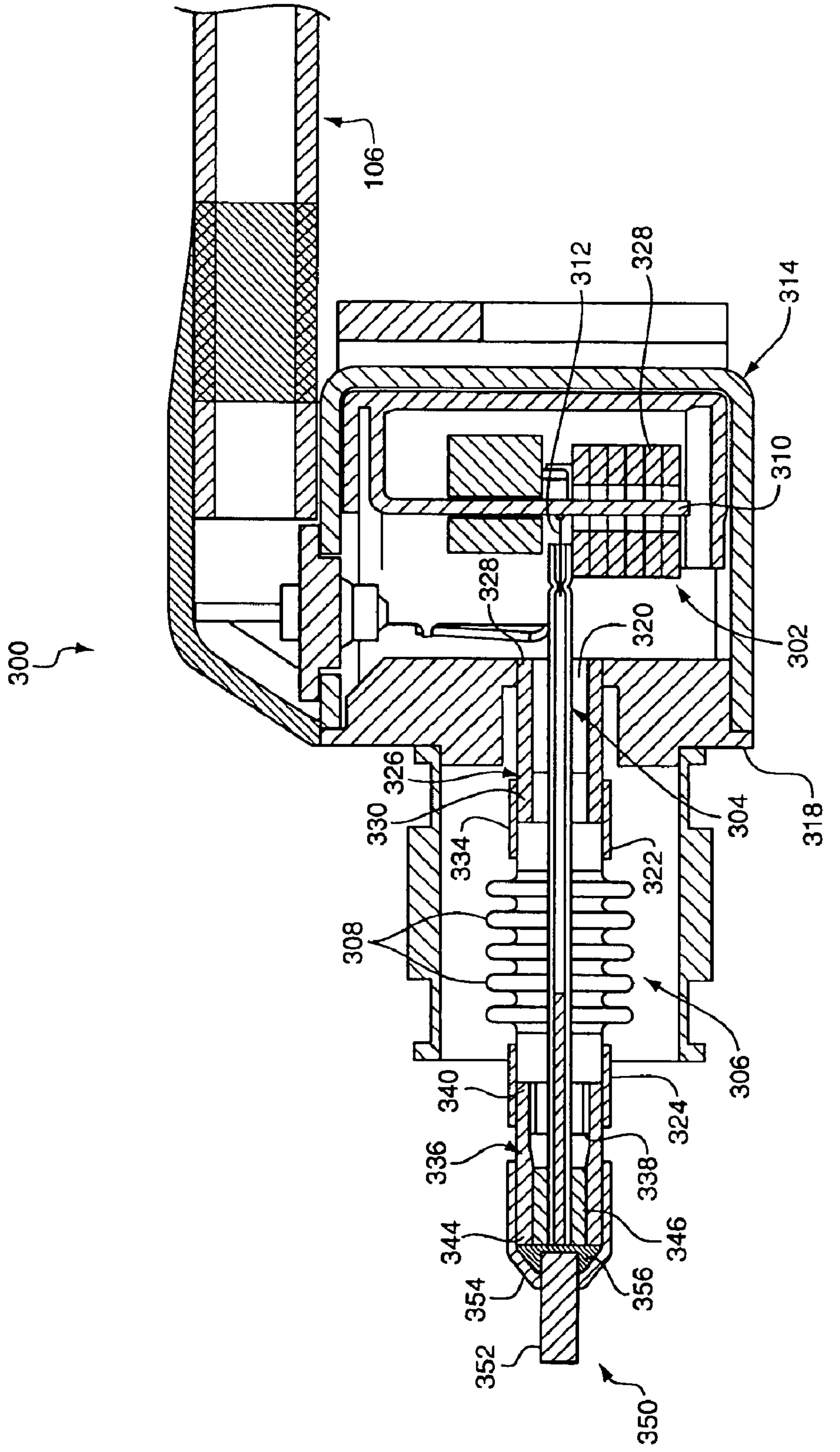
FIG. 3 illustrates an example of a hearing aid transducer according to the present invention.

Hearing Aid Transducer:

FIG. 3 illustrates one example of the transducer 108, namely transducer 300 including an actuator interface 356. The transducer 300 may be employed in either a semi-implantable or fully-implantable hearing aid device. The transducer 300 includes an electromechanical driver 302, an elongated vibratory member 304 interconnected at a proximal end to the driver 302, and a hollow bellows 306 interconnected to a distal end of the vibratory member 304. In use, the vibratory member 304 induces axial vibrations which are in turn communicated to the incus 120 of the ossicles via an actuator 352 to yield enhanced hearing. Bellows 306 comprises a plurality of undulations 308 that allow bellows 306 to axially respond in an accordion-like fashion to axial vibrations of the vibratory member 304. Of note, bellows 306 is sealed to provide for isolation of the internal componentry of transducer 300.

The electromechanical driver 302 comprises a leaf 310 extending through a plurality of coils 358. Coils 358 may be electrically interconnected to the wire 106, which provides signals that induce a desired magnetic field across coils 358 to affect desired movement of leaf 310. In the illustrated embodiment, leaf 310 is connected to a stiff wire 312, and vibratory member 304 is crimped onto the wire 312. As such, movement of leaf 310 affects axial vibration of vibratory member 304.

Driver 302 is disposed within a housing 314, comprising a welded main body and lid housing member 318. In order to affect the communication of axial vibrations, vibratory member 304 passes through an opening 320 of the lid member 318 and extends through the bellows 306. To maintain isolation of driver 302 within housing 314, bellows 306 is hermetically sealed and hermetically interconnected to the housing 314 at its proximal end 322 and to the vibratory member 304 at its distal end 324.

More particularly, a proximal sleeve 326 may be welded at its proximal end 328 to lid member 318 about the opening 320. Preferably, proximal sleeve 326 and housing member 318 all comprise the same biocompatible metal, such as, titanium, a titanium alloy, platinum, a platinum alloy, or gold-plated stainless steel. An end portion, or tang 332, of the proximal end 322 of bellows 306 is slidably and intimately disposed within a cylindrical distal end 330 of proximal sleeve 326. As shown, the proximal end 322 of bellows 306 may be of a stepped-in, cylindrical configuration; wherein the distal end 330 of proximal sleeve 326 may abut the bellows 306 to define a substantially flush, annular interface region therebetween. Such an arrangement accommodates the application and reliability of an overlapping electrodeposited layer 334 (e.g., comprising a biocompatible material such as gold) disposed across and about the abutment region for interconnection and sealing purposes.

Similarly, a distal sleeve 336 may be slidably and intimately disposed about an end portion, or tang 338, of the distal end 324 of bellows 306. The distal end 324 may be of a stepped-in, cylindrical configuration, to define the tang 338, wherein a cylindrical proximal end 340 of distal sleeve 336 may abut the bellows 306 to define a substantially flush, annular interface region therebetween. Again, a reliable overlapping electrodeposited layer (e.g., comprising a biocompatible material such as gold) may be readily provided across and about the abutment region for interconnection and sealing purposes.

In the illustrated embodiment, a cylindrical distal end 344 of distal sleeve 336 receives a cylindrical bushing 346, which locates the distal end of vibratory member 304 therewithin. As further shown, the distal end portion of vibratory member 304 is disposed within the distal sleeve 336 such that the distal extreme of distal sleeve 336, bushing 346, and vibratory member 304 collectively provide a substantially uninterrupted surface. In this regard, a fusion weld interconnection (e.g., as may be achieved by laser welding) may be provided between the sleeve 336 and bushing 346, to seal the distal end of distal sleeve 346 and bellows 306.

The transducer 300 also includes a tip assembly 350 having an interconnected actuator 352, cap member 354, and actuator interface 356 disposed within the cap member 354 around the actuator 352. The cap member 354 may be interconnected (e.g., via tack welding) about the distal end 344 of distal sleeve 336. As will be further described below, the actuator interface 356 permits movement of the actuator 352 both axially and rotationally relative to the cap member 354 to relax or minimize loading of the incus 120 by the transducer 300. In this regard, the actuator 352 may be particularly adapted for tissue attachment with the ossicles of the patient, such as construction with a ceramic material or coated therewith.

Figure 4:
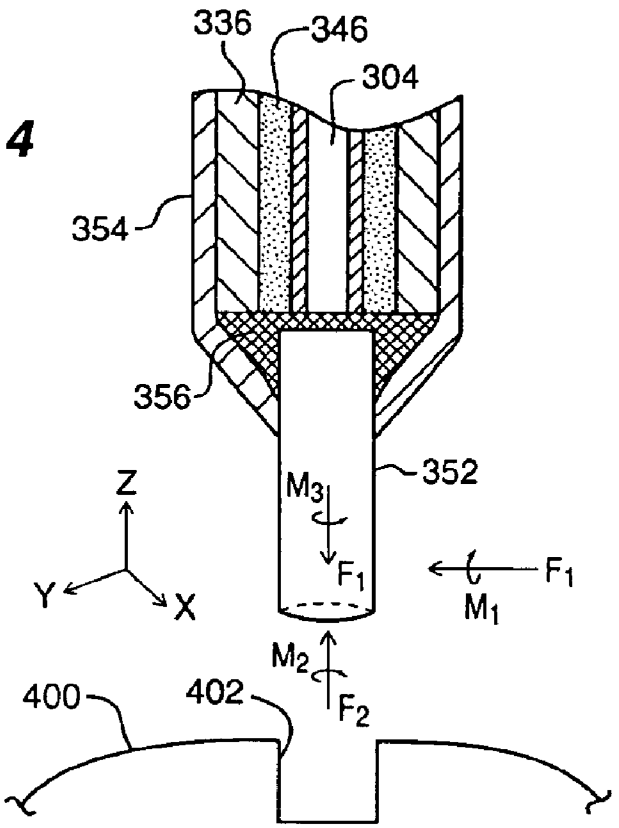
FIGS. 4 and 5 illustrate additional details with regard to the hearing aid transducer of FIG. 3.

Referring to FIG. 4, the actuator 352 is designed to couple with the ossicles and specifically the incus 120 of the patient. In one example, the actuator 352 may couple with a mating aperture 402 formed in the incus 120 during implantation of the transducer 300. In this regard, the actuator 352 is supported within the cap member 354 by the actuator interface 356 such that the actuator interface 356 is disposed around the actuator 352 within the cap member 354.

In one embodiment of the transducer 300, the actuator interface 356 may comprise a material that is reshapeable at body temperature such that it relaxes under light loading, e.g., a steady state application of pressure from the incus 120. Additionally, the material of the actuator interface 356 should be chosen such that it is viscous enough to resist sudden movements of the actuator 352 by the vibratory member 304 to permit the transfer of mechanical energy at audible frequencies from the vibratory member 304 to the actuator 352 and the incus 120. In this regard, the actuator interface 356 may be any suitable material with the above-described properties. Some examples of the actuator interface 356 include materials that exhibit permanent fluid properties such that they are reshapeable or retain their ability to "cold flow." More particularly, some examples of the actuator interface 356 include bone wax, Teflon, and/or silicon based elastomer, although those skilled in the art will appreciate numerous other suitable materials according to the principles of the present invention. It will also be appreciated that the cold flowing or reshapeable properties of such materials may be altered such that the actuator interface 356 permits compensating movement of the actuator 352 when the pressure on the actuator 352 reaches a predetermined threshold. For instance, it may be desirable to configure the actuator interface 356 such that it is responsive, e.g., permits movement of the actuator 352 when the pressure is in the range of 0.1 pound per square inch (PSI) to 1 PSI and more preferably in the range of 0.1 PSI to 0.5 PSI.

Operationally, if a load is imposed on the actuator 352 by the incus 120, the actuator interface 356 relaxes permitting movement of the actuator 352 within the cap member 354 toward a state of equilibrium to relax the load. For instance, in the case of a movement of the incus 120 in the direction of the force F1, e.g., which also applies the force F1 on the actuator 352, the actuator 352 moves tangentially along the (X) axis to minimize loading on the incus 120. Similarly, in the case of movement of the incus 120 in a direction of the force F2, e.g., which also applies the force F2 on the actuator 352, the actuator 352 moves axially along the (Y) axis to minimize loading on the incus 120. Finally, in the case of movement of the incus 120 in a direction of the force F3, e.g., which also applies the force F3 on the actuator 352, the actuator 352 moves along the (Z) axis to minimize loading on the incus 120. Furthermore, as will be appreciated, combinations of such movements result in combinations of forces and/or moments, e.g., moments M1–M3, which produce responsive movements of the actuator 352 to minimize loading on the incus 120.

In another embodiment of the transducer 300, the actuator interface 356 may be a material that is easily reshapeable under light loading and that is curable to a solid or semi-solid state. For instance, the actuator interface 356 may be a liquid, gel, or other soft material that is curable with a stimulus such as heat or a chemical catalyst to a solid state. Operationally, during the implant procedure, if the actuator 352 is connected to the aperture 402, such that a load force, e.g., F1–F3, due to axial, radial, or torsional misalignments of the transducer 300 is imposed on the incus 120, the actuator interface 356 relaxes permitting movement of the actuator 352 within the cap member 354 toward a state of equilibrium. Once an equilibrium state is reached and forces F1–F3 or moments M1–M3 are relaxed, the actuator interface 356 may be cured to fix the actuator 352 in position relative to the cap member 354 and incus 120. Unlike the above embodiment, this embodiment does not provide the advantage of providing continuous compensation for movements of the incus 120, but does provide the advantage of initially providing a proper interface between the incus 120 and transducer 300. Some examples of materials according to this embodiment include without limitation, bone wax, epoxy, or materials conventionally utilized in the dental profession, curable with light, air, moisture etc.

In another embodiment of the transducer 300, the actuator interface 356 may be a material that is initially in a soft state such that the actuator 352 is free to move relative to the cap member 354. Subsequent to positioning of the transducer 300 and connection of the actuator 352 to the incus 120, however, the actuator interface 356 may be transformed using a stimulus, such as heat, to a higher viscosity material capable of transmitting vibrations at audible frequencies but also permitting gradual movement of the actuator 352 in response to pressure from the incus 120. Some examples of materials according to this embodiment include without limitation, bone wax, and Teflon based materials.

Alternatively, it will be appreciated that the actuator interface 356 may be a material that is initially in a solid or semi-solid state and that is alterable to a softened state With a stimulus, e.g., heat. In this regard, the actuator 352 may be connected to the aperture 402 prior to application of the stimulus. Upon application of the stimulus loading pressures between the actuator 352 and incus 120 may be relaxed. Upon relaxation of the loading pressures, the stimulus may be removed permitting the actuator interface 356 to again solidify or substantially solidify to permit transmission of mechanical energy to the incus 120 via the actuator 352 at audible frequencies. Some examples of materials according to this embodiment include without limitation, wax based materials, and/or silicone based materials.

Figure 5:
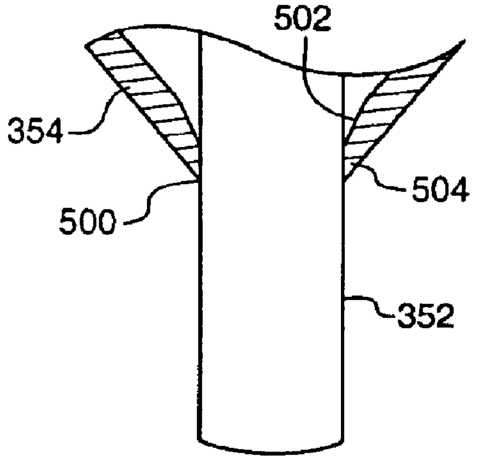

Referring to FIGS. 5, the cap member 354 includes an annular orifice 500 for receipt of the actuator 352. The orifice 500 includes a distal portion 504 configured to form an annular compression seal about the actuator 352. A proximate portion 502 is angled or beveled to permit axial and or radial movement of the actuator 352 relative to and within the cap member 354. In this characterization, the cap member 354 provides a seal to prevent the escape of the actuator interface 356 while at the same time permitting movement of the actuator 352 relative to the transducer 300 and specifically the cap member 354.

Figure 6:
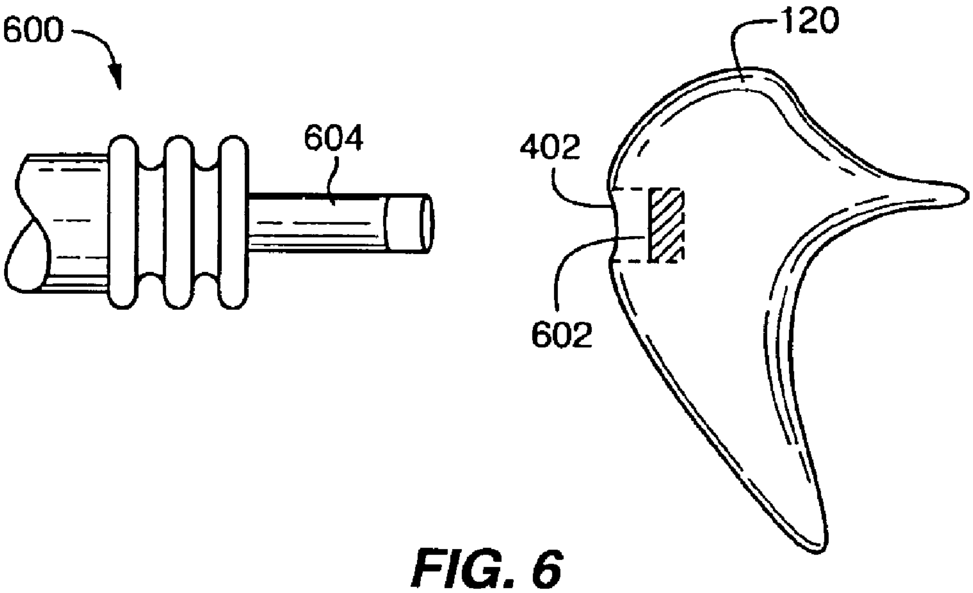
FIG. 6 illustrates another example of a hearing aid transducer according to the present invention.

FIG. 6 illustrates another example of the transducer 108, namely transducer 600. Transducer 600 is similar to the transducer 300 in that it includes a driver (not shown) for inducing stimulating movement of an actuator 604 to enhance or produce the sensation of sound through the natural movements of the ossicles, e.g., the incus 120. In this regard, the transducer 600 also includes an actuator interface 602 located between the actuator 604 and the incus 120. In one example according to this embodiment, the actuator interface 602 may be located within the aperture 402 that serves as an interface for the attachment of the actuator 604. Advantageously, according to this characterization, the actuator interface 602 may serve the dual purpose of retaining the actuator 604 within the aperture 402, while permitting gradual movement of the incus 120 relative to the transducer 600. The actuator interface 602 may comprise any suitable material that relaxes under light constant loading at body temperature, e.g., steady state application of pressure by the incus 120, yet remains resistive to sudden movements of the actuator 604 to permit efficient mechanical energy transfer at audible frequencies. Preferably, as with the above embodiment, the actuator interface 356 is a biocompatible material and may include materials such as bone wax, Teflon, and/or silicon based elastomer, that exhibit permanent fluid properties such that they are reshapeable to compensate for loading pressures.

The actuator interface material may also be a material that changes state in response to a stimulus as described above. Specifically, in this regard, the actuator interface material may be 1) a material that is easily displaceable under light loading and that is curable to a solid or semi-solid state, 2) a material selectively transformable from an initially soft state to a state that permits mechanical energy transfer at audible frequencies but that is still reshapeable to compensate for loading pressures, and/or 3) a material that is initially in a solid or semi-solid state and that is alterable to a softened state with a stimulus, e.g., heat, and then alterable back to the substantially solid state.

Figure 7:
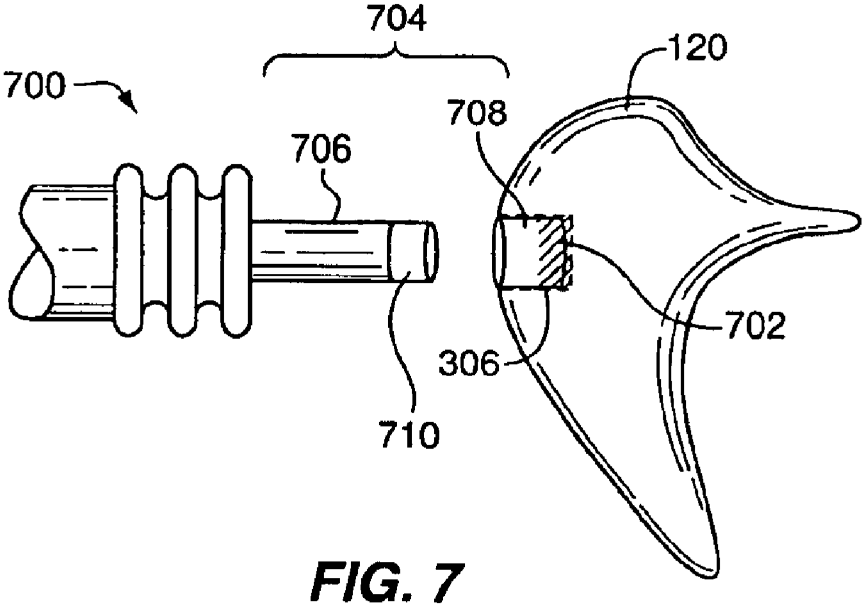
FIG. 7 illustrates another example of a hearing aid transducer according to the present invention.

FIG. 7 illustrates another example of the transducer 108, namely transducer 700. Transducer 700 is similar to the transducer 600 in that it includes a driver (not shown) for inducing stimulating movement of an actuator 704 to enhance or produce the sensation of sound through the natural movements of the ossicles, e.g., the incus 120. In this embodiment, however, the actuator 704 includes a first portion 706 connected to the driver of the transducer 700 and a second portion 708 connectable to a middle ear component, e.g., incus 120. According to this characterization, the actuator portion 708 may be configured in the shape of a sleeve sized to receive a tip 710 of the actuator portion 706.

The transducer 700 also includes an actuator interface 702 located between the first portion 706 and the second portion 708 of the actuator 704, and specifically, within the sleeve portion 702. As with the above embodiments, the actuator interface 702 may comprise numerous materials having one or more of the above-described properties. In addition, as with the above embodiment, the actuator interface 702 may also serve the dual purpose of retaining the tip 710 of the actuator portion 706 within the sleeve portion 708 of the actuator 704, while permitting gradual movement of the incus 120 relative to the transducer 700.

Those skilled in the art will appreciate variations of the above-described embodiments that fall within the scope of the invention. As a result, the invention is not limited to the specific examples and illustrations discussed above, but only by the following claims and their equivalents.

We claim:

1. An implantable hearing aid transducer comprising:

an actuator to stimulate a middle ear component to produce a sensation of sound;

a driver to drive the actuator in response to transducer drive signals; and an actuator interface for interconnecting a first portion of the actuator to at least one of the driver, the middle ear component and a second portion of the actuator, wherein the actuator interface material is reshapeable in situ from a first shape to a second shape, in response to a pressure between the actuator and the middle ear component, to permit movement of one of the actuator and the middle ear component in at least a first dimension to reduce loading therebetween.

2. The transducer of claim 1, wherein when the transducer is implanted in a patient, the actuator interface comprises a material that is automatically reshapeable from the first shape to the second shape in response to the pressure.

3. The transducer of claim 1, wherein the actuator interface comprises a material that transmits vibration at acoustic frequencies between the actuator and the middle ear component.

4. The transducer of claim 1, wherein the actuator interface maintains the first shape until the pressure is greater than a pre-determined threshold whereupon the actuator interface assumes the second shape.

5. The transducer of claim 1, wherein the actuator interface is selectively reshapeable from the first shape to the second shape in response to the pressure and further in response to a stimulus that initiates the reshaping from the first shape to the second shape.

6. The transducer of claim 5, wherein the actuator interface is substantially solid and becomes deformable in response to the stimulus.

7. The transducer of claim 5, wherein the actuator interface is deformable and becomes substantially solid in response to the stimulus.

8. The transducer of claim 5, wherein the actuator interface comprises a material that is selectively reshapeable in response to a heat stimulus.

9. The transducer of claim 5, wherein the actuator interface comprises a material that is selectively reshapeable in response to a chemical stimulus.

10. The transducer of claim 1, wherein the actuator interface comprises a material that is selectively reshapeable in response to a light stimulus.

11. The transducer of claim 1, wherein the actuator interface permits movement of the actuator in a second dimension relative to the middle ear component.

12. The transducer of claim 1, wherein the actuator interface comprises:

a wax based material.

13. The transducer of claim 1, wherein the actuator interface comprises:

an elastomer based material.

14. The transducer of claim 1, wherein the actuator interface comprises:

a silicon based material.

15. A method for preventing loading of a middle ear component by an implantable hearing aid transducer, the method comprising coupling an actuator of the transducer to the middle ear component using at least one actuator interface disposed between a first portion of the actuator and at least one a driver of the transducer, the middle ear component and a second portion of the actuator; and in response to a pressure between the actuator and the middle ear component, reshaping in situ the actuator interface from a first shape to a second shape to permit movement of one of the actuator and the middle ear component in at least a first dimension.

16. The method of claim 15, wherein the reshaping step comprises:

reshaping the actuator interface in response to pressure above a predetermined threshold.

17. The method of claim 15, wherein the reshaping step comprises:

automatically reshaping the actuator interface from the first shape to the second shape in response to the pressure.

18. The method of claim 15, wherein the reshaping step comprises:

providing a stimulus to the actuator interface to initiate the reshaping from the first shape to the second shape.

19. The method of claim 18, the method further comprising:

responsive to the stimulus, transforming the actuator interface from a solid state to a deformable state.

20. The method of claim 18, the method further comprising:

responsive to the stimulus, transforming the actuator interface from a deformable state to a solid state.

21. The method of claim 15, wherein the reshaping step comprises:

reshaping the actuator interface from the first shape to the second shape to permit movement of one of the actuator and the middle ear component in a second dimension.

22. The method of claim 18, wherein providing a stimulus comprises providing a heat stimulus.

23. The method of claim 18, wherein providing a stimulus comprises providing a chemical stimulus.

24. The method of claim 18, wherein providing a stimulus comprises providing a light stimulus.

25. A hearing aid comprising:

an acoustic signal receiver to receive acoustic sound and generate acoustic response signals;

a signal processor to process the acoustic response signals to generate transducer drive signals;

a transducer comprising:

- an actuator to stimulate a middle ear component and produce a sensation of sound;
- a driver to drive the actuator in response to the transducer drive signals; and
- an actuator interface material for interconnecting a first portion of the actuator to at least one of the driver, the middle ear component and a second portion of the actuator, wherein the actuator interface material is reshapeable in situ from a first shape to a second shape, in response to a pressure between the actuator and the middle ear component, to permit movement of one of the actuator and the middle ear component in at least a first dimension.

26. The hearing aid of claim 25, wherein the actuator interface is reshapeable in situ from the first shape to the second shape to permit movement of one of the actuator and the middle ear component in at least a second dimension.

* * * * *